United States Patent
Eichhorn et al.

(10) Patent No.: US 11,106,726 B2
(45) Date of Patent: Aug. 31, 2021

(54) SYSTEMS AND METHODS FOR AN IMAGE REPOSITORY FOR PATHOLOGY

(71) Applicant: LEICA BIOSYSTEMS IMAGING, INC., Vista, CA (US)

(72) Inventors: Ole Eichhorn, Westlake Village, CA (US); Dirk Soenksen, Carlsbad, CA (US)

(73) Assignee: Leica Biosystems Imaging, Inc., Vista, CA (US)

(*) Notice: Subject to any disclaimer, the term of this patent is extended or adjusted under 35 U.S.C. 154(b) by 0 days.

(21) Appl. No.: 16/902,086

(22) Filed: Jun. 15, 2020

(65) Prior Publication Data

US 2020/0311127 A1 Oct. 1, 2020

Related U.S. Application Data

(63) Continuation of application No. 14/437,821, filed as application No. PCT/US2013/032293 on Mar. 15, 2013, now Pat. No. 10,685,056.

(Continued)

(51) Int. Cl.
*G06F 16/58* (2019.01)
*G06F 16/54* (2019.01)
(Continued)

(52) U.S. Cl.
CPC .......... *G06F 16/5866* (2019.01); *G06F 16/54* (2019.01); *G06Q 10/10* (2013.01);
(Continued)

(58) Field of Classification Search
CPC ..... G06F 16/54; G06F 16/5866; G16Z 99/00; G06Q 20/145; G06Q 10/10; G06Q 30/06; G16H 70/00; G16H 30/20; G16H 30/40
See application file for complete search history.

(56) References Cited

U.S. PATENT DOCUMENTS 5,493,677 A  2/1996 Balogh et al.
5,893,095 A  4/1999 Jain et al.
(Continued)

FOREIGN PATENT DOCUMENTS

JP  2003-271617 A  9/2003
JP  2009-245315 A  10/2009
(Continued)

OTHER PUBLICATIONS

Leong et al., "Digital photography in anatomical pathology", J Postgrad Med. (2004) 50(1):62-69.
(Continued)

*Primary Examiner* — Brittany N Allen
(74) *Attorney, Agent, or Firm* — Knobbe, Martens, Olson & Bear, LLP

(57) ABSTRACT

Systems and methods for managing an image repository for pathology. In an embodiment, a search request is received. One or more digital slide images are identified from an image repository based on the search request. A user is provided access to the identified digital slide images. In addition, each of a plurality of collections of digital slide images are associated with a search rating, and a value for each of the plurality of collections is computed based on the associated search rating and a size of the collection.

20 Claims, 4 Drawing Sheets

Related U.S. Application Data

(60) Provisional application No. 61/717,557, filed on Oct. 23, 2012.

(51) Int. Cl.

| | | |
|---|---|---|
| *G06Q 10/10* | (2012.01) | |
| *G06Q 30/06* | (2012.01) | |
| *G16H 30/20* | (2018.01) | |
| *G16H 30/40* | (2018.01) | |
| *G16H 70/00* | (2018.01) | |
| *G06Q 20/14* | (2012.01) | |
| *G16Z 99/00* | (2019.01) | |

(52) U.S. Cl.
CPC .......... *G06Q 20/145* (2013.01); *G06Q 30/06* (2013.01); *G16H 30/20* (2018.01); *G16H 30/40* (2018.01); *G16H 70/00* (2018.01); *G16Z 99/00* (2019.02)

(56) References Cited

U.S. PATENT DOCUMENTS

| | | | |
|---|---|---|---|
| 7,099,860 | B1 | 8/2006 | Liu et al. |
| 7,752,251 | B1 | 7/2010 | Shuster et al. |
| 8,156,123 | B2 * | 4/2012 | Tribble ............. G06F 16/90335 707/739 |
| 8,713,592 | B2 | 4/2014 | Patterson et al. |
| 8,761,512 | B1 | 6/2014 | Buddemeier et al. |
| 9,277,184 | B2 | 3/2016 | Dupree |
| 9,330,071 | B1 | 5/2016 | Ahmed et al. |
| 9,483,788 | B2 | 11/2016 | Martin |
| 9,760,547 | B1 | 9/2017 | Brougher et al. |
| 2002/0198866 | A1 | 12/2002 | Kraft et al. |
| 2004/0225577 | A1 | 11/2004 | Robinson |
| 2004/0267740 | A1 | 12/2004 | Liu et al. |
| 2005/0055344 | A1 | 3/2005 | Liu et al. |
| 2005/0114325 | A1 | 5/2005 | Liu et al. |
| 2006/0204142 | A1 | 9/2006 | West et al. |
| 2007/0118802 | A1 | 5/2007 | Gerace et al. |
| 2007/0174872 | A1 | 7/2007 | Jing et al. |
| 2010/0048242 | A1 | 2/2010 | Rhoads et al. |
| 2010/0082650 | A1 | 4/2010 | Wong |
| 2010/0332401 | A1 | 12/2010 | Prahlad et al. |
| 2011/0022658 | A1 | 1/2011 | Pace et al. |
| 2011/0060766 | A1 | 3/2011 | Ehlke et al. |
| 2011/0125791 | A1 * | 5/2011 | Konig ................... G06F 16/951 707/770 |
| 2012/0109955 | A1 | 5/2012 | Lahcanski et al. |
| 2013/0217440 | A1 | 8/2013 | Lord et al. |
| 2013/0273968 | A1 | 10/2013 | Rhoads et al. |
| 2013/0295894 | A1 | 11/2013 | Rhoads et al. |
| 2013/0346501 | A1 | 12/2013 | Hardas et al. |
| 2015/0022675 | A1 | 1/2015 | Lord et al. |

FOREIGN PATENT DOCUMENTS

| | | |
|---|---|---|
| KR | 1020090097710 A | 9/2009 |
| WO | 2014065868 A1 | 5/2014 |

OTHER PUBLICATIONS

Muller, H et al., "A review of content-based image retrieval systems in medical applications—clinical benefits and future directions", International Journal of Medical Informatics, Elsevier Scientific Publishers, Shannon, IR (2004) 73(1):1-23, in 24 pages.

Carey, 15 Stock Photography Sites to Sell Your Photos—for Beginners and Pros, Jan. 5, 2010 (Year: 2010).

Extended European Search Report dated Jun. 17, 2016 for related European Patent Application No. 13849222.8, in 10 pages.

International Search Report and Written Opinion for related International Application No. PCTUS2013032293 dated Jul. 18, 2013, in 13 pages.

Communication pursuant to Article 94(3) EPC dated Jun. 22, 2017 for related European Patent Application No. 13849222.8, in 7 pages.

* cited by examiner

SYSTEMS AND METHODS FOR AN IMAGE REPOSITORY FOR PATHOLOGY

CROSS-REFERENCE TO RELATED APPLICATIONS

The present application is a continuation of U.S. patent application Ser. No. 14/437,821, filed on Apr. 22, 2015, which is the U.S. national stage application of International Patent Application No. PCT/US2013/032293, filed on Mar. 15, 2013, which claims priority to U.S. Provisional Patent Application No. 61/717,557, filed on Oct. 23, 2012, which are all hereby incorporated herein by reference as if set forth in full.

FIELD OF THE INVENTION

The systems and methods disclosed herein generally relate to a repository and software application for storing, managing, and searching digital slide images for pathology.

BACKGROUND

Many pathology specimens are prepared as glass slides, in preparation for examination with optical microscopy. Large collections of glass slides, such as the Juan Rosai Collection, represent extremely valuable bodies of knowledge. However, slides are subject to breakage, being lost, having their stains bleach over time, having the tissue deteriorate, and other processes which degrade or destroy the information they contain. In addition, collections of glass slides require significant physical storage space and the cabinets holding such collections are heavy, thereby limiting the locations in which they can be placed. Physical slide collections are also difficult to search for information. Expensive external systems are often required to index slides and maintain the information systems which describe their contents. The nature of physical slide collections also limit access to them, since anyone who wishes to examine the information on a slide must be in the same physical location as the slide. Shipping slides to share their information is expensive and removes them from the collection, preventing anyone else from accessing them. Furthermore, physical slide collections are often distributed across different physical locations. This makes it difficult for students, educators, pathologists, scientists, and others to search for information across multiple collections.

Digitizing physical slide collections holds the promise of indefinitely preserving the information contained in such collections. However, such digital collections are still distributed in nature (e.g., across numerous, disparate information systems of multiple, unrelated laboratories, hospitals, etc.), making it difficult to search across multiple collections. What is needed is a system or method for aggregating, organizing, and managing digital slide collections, so that they may be easily and efficiently searched and otherwise utilized.

SUMMARY

In an embodiment, a system for managing an image repository for pathology is disclosed. The system comprises: at least one hardware processor; a memory; an image repository stored on the memory, the image repository comprising a plurality of collections, wherein each of the plurality of collections comprises one or more digital slide images and associated metadata; and at least one executable software module that, when executed by the at least one hardware processor, receives a search request, identifies one or more digital slide images based on at least the search request, provides access to the identified one or more digital slide images to a user, associates each of the plurality of collections with a search rating, and computes a value for each of the plurality of collections based on the associated search rating and a size of the collection.

In an additional embodiment, a method for managing an image repository for pathology is disclosed. The method comprises, using at least one hardware processor: providing an image repository, the image repository comprising a plurality of collections, wherein each of the plurality of collections comprises one or more digital slide images and associated metadata; receiving a search request; identifying one or more digital slide images based on at least the search request; providing access to the identified one or more digital slide images to a user; associating each of the plurality of collections with a search rating; and computing a value for each of the plurality of collections based on the associated search rating and a size of the collection.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Systems and methods for managing an image repository for pathology are disclosed.

System Overview

Figure 1:
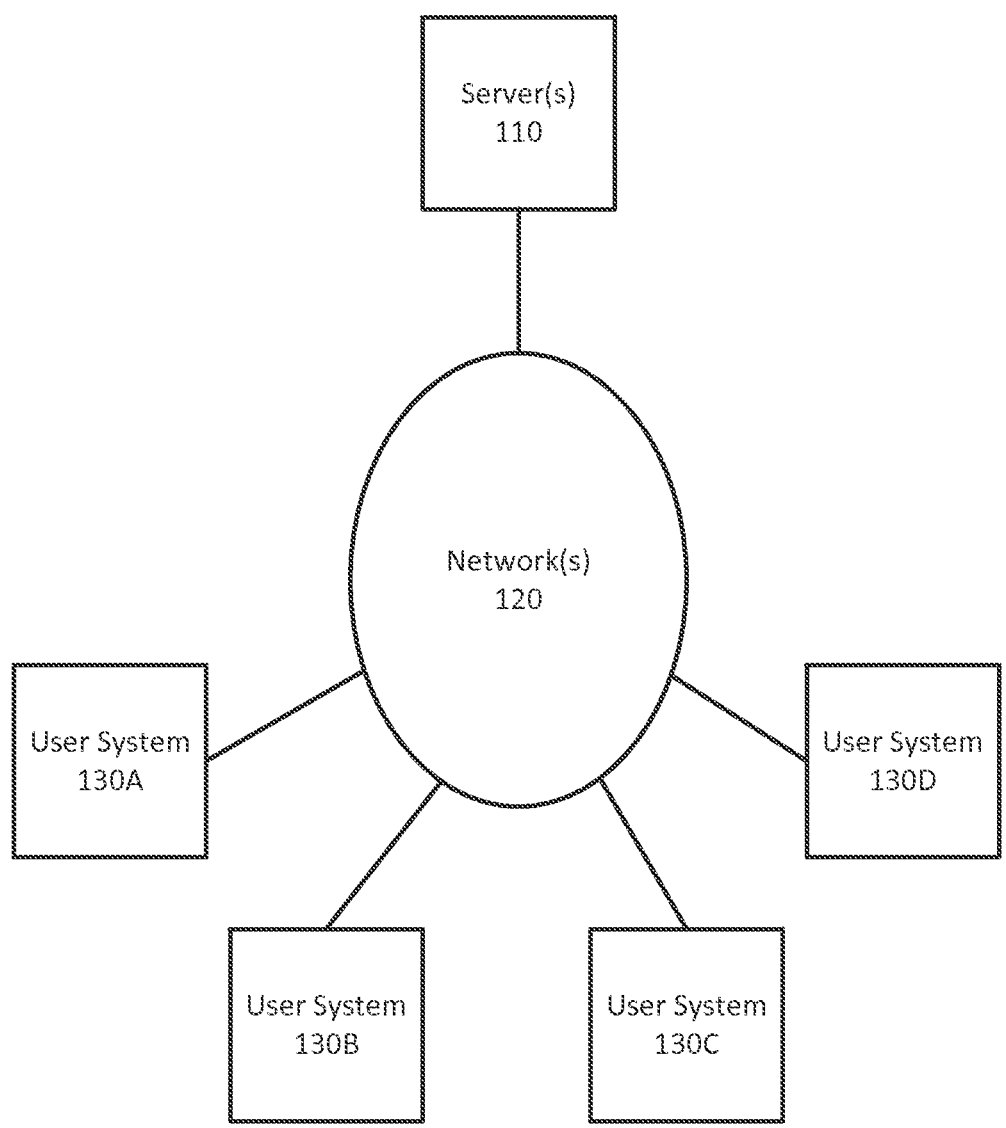
FIG. 1 illustrates a system for managing an image repository, according to an embodiment.

FIG. 1 illustrates an example system for managing an image repository for pathology, according to an embodiment. The system may comprise a set or platform of one or more servers 110 which host and/or execute one or more of the various functions, processes, and/or software modules described herein. In addition, server(s) 110 are communicatively connected to one or more user systems 130 via one or more network(s) 120. Network(s) 120 may comprise the Internet, and server(s) 110 may communicate with user system(s) 130 through the Internet using standard transmission protocols, such as HyperText Transfer Protocol (HTTP), Secure HTTP (HTTPS), File Transfer Protocol (FTP), FTP Secure (FTPS), SSH FTP (SFTP), and the like, as well as proprietary protocols. In an embodiment, server(s) 110 may not be dedicated servers, and may instead be cloud instances, which utilize shared resources of one or more servers. Furthermore, while server(s) 110 are illustrated as being connected to various systems through a single set of network(s) 120, it should be understood that server(s) 110 may be connected to the various systems via different sets of one or more networks. For example, server(s) 110 may be connected to a subset of user systems 130 via the Internet, but may be connected to one or more other user systems 130 via an intranet. It should also be understood that user system(s) 130 may comprise any type or types of computing devices capable of wired and/or wireless communication, including without limitation, desktop computers, laptop computers, tablet computers, smart phones or other mobile phones, servers, game consoles, televisions, set-top boxes, electronic kiosks, Automated Teller Machines, and the like. In addition, while only a few user systems 130 and one set of server(s) 110 are illustrated, it should be understood that the network may comprise any number of user systems and sets of server(s).

Server(s) 110 may comprise web servers which host one or more websites or web services. In embodiments in which a website is provided, the website may comprise one or more user interfaces, including, for example, web pages generated in HyperText Markup Language (HTML) or other language. Server(s) 110 transmit or serve these user interfaces in response to requests from user system(s) 130. In some embodiments, these user interfaces may be served in the form of a wizard, in which case two or more user interfaces may be served in a sequential manner, and one or more of the sequential user interfaces may depend on an interaction of the user or user system with one or more preceding user interfaces. The requests to server(s) 110 and the responses from server(s) 110, including the user interfaces, may both be communicated through network(s) 120, which may include the Internet, using standard communication protocols (e.g., HTTP, HTTPS). These user interfaces or web pages may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases (not shown) that are locally and/or remotely accessible to the server(s) 110. Server(s) 110 may also respond to other requests from user system(s) 130.

Server(s) 110 may comprise, be communicatively coupled with, or otherwise have access to one or more database(s). For example, server(s) 110 may comprise one or more database servers which manage one or more databases. A user system 130 or application executing on server(s) 110 may submit data (e.g., user data, form data, etc.) to be stored in the database(s), and/or request access to data stored in such database(s). Any suitable database may be utilized, including without limitation MySQL, Oracle, IBM, Microsoft SQL, Sybase, Access, and the like, including cloud-based database instances. Data may be sent to the server(s) 110, for instance, using the well-known POST request supported by HTTP, via FTP, etc. This data, as well as other requests, may be handled, for example, by server-side web technology, such as a servlet or other software module, executed by server(s) 110.

In embodiments in which a web service is provided, server(s) 110 may receive requests from user system(s) 130, and provide responses in eXtensible Markup Language (XML) and/or any other suitable or desired format. In such embodiments, server(s) 110 may provide an application programming interface (API) which defines the manner in which user system(s) 130 may interact with the web service. Thus, user system(s) 130, which may themselves be servers, can define their own user interfaces, and rely on the web service to implement the backend processes, functionality, storage, etc., described herein. For example, in such an embodiment, a client application executing on one or more user system(s) 130 may interact with a server application executing on server(s) 110 to execute one or more or a portion of one or more of the various functions, processes, and/or software modules described herein. The client application may be "thin," in which case processing is primarily carried out server-side by server(s) 110. A simple example of a thin client application is a browser application, which simply requests, receives, and renders web pages at user system(s) 130, while server(s) 110 are responsible for generating the web pages and managing database functions. Alternatively, the client application may be "thick," in which case processing is primarily carried out client-side by user system(s) 130. It should be understood that the client application may perform an amount of processing, relative to server(s) 110, at any point along this spectrum between "thin" and "thick," depending on the design goals of the particular implementation. In any case, the application, which may wholly reside on either the server(s) or user system(s) or be distributed between the server(s) or user system(s), can comprise one or more executable software modules that implement one or more of the processes or functions of the application(s) described herein.

In an embodiment, server(s) or server platform 110 hosts and/or executes one or more software modules, including a web application. The web application comprises one or more user interfaces which provides access to a web-hosted image repository. The image repository may comprise collections of slide images (e.g., whole-slide images or partial-slide images) together with metadata associated with those collections and/or the individual slide images. The metadata associated with collections and images may consist of technical information about the images, such as resolution, dimensions, color space descriptions, specimen information, patient case histories, experiment details, publication details, and any other descriptions of the images and descriptions of the samples represented by the images. The collections may comprise private and public collections. According to an embodiment, the slide images comprise slide images for pathology, i.e., the study of the origin, nature, and course of diseases.

In an embodiment, the software modules of server platform 110 comprise a robust search engine that enables searching of the collections and slide images. In the case of pathology slide images, this may enable examples of particular medical conditions to be easily found. The search engine may also provide a unique and powerful resource for education and/or clinical decision support for pathologists, clinicians, scientists, educators, and/or students.

Roles

In an embodiment, access to the repository or certain data within the repository is either granted or denied based on one or more roles. The roles may comprise a group of one or more permissions, and describe user and partner relationships. Permissions define an action that a user is able to perform with the repository. Users can be individuals or institutions. In an embodiment, the roles may represent one or more of a user, curator, contributor, host, authentication provider, and tool provider. Each role may correspond to a relationship which has business rules, a technical implementation, and/or a cost model.

Free and Subscribed Users

In an embodiment, use of the repository may be free or by subscription (e.g., monthly or annual subscription). Free users (i.e., users using the repository for free) may be given access to all content in public collections of the repository, but such access may be restricted to viewing images at a limited resolution (e.g., up to 5× resolution). Subscribed users, on the other hand, may be given access to all content at full resolution. In an embodiment, when a free user views an image via the web application, the web application may provide the free user the option to pay a transaction fee to view the image at full resolution and/or to subscribe to the repository and thereby view all images at full resolution.

Owned Collections with Various Access Models

Content in the repository comprises slide images (or "eSlides") with metadata. These slide images and associated metadata are organized into collections. Each collection may have owner(s), administrator(s), and/or curator(s), and may be associated with profile information.

In an embodiment, most collections may be public collections, which are available to all users of the repository (e.g., whether or not they have paid a subscription fee). One or more software modules of server platform 110 may compute a value for each public collection based on the collection's ratio of its search rating to its hosting size. Depending and based on a collection's computed value, either (a) the collection may earn money for its owner(s), or (b) maintenance of the collection may cost the owner(s) a hosting fee.

In an embodiment, an owner of a collection may designate the collection as a premium collection (e.g., through one or more user interfaces of the web application). If a collection is designated as premium, then, in order to have access to the collection, a user must subscribe separately to the collection or pay for access (e.g., on a per-view basis). Owner(s) of a premium collection may be required to pay a hosting fee (e.g., based on storage size of the collection). Owner(s) of a premium collection may also be required to share the premium subscription fees or per-view revenue fees received for a premium collection with an operator of the repository (e.g., on a percentage basis or as a fixed fee).

In an embodiment, an owner of a collection may designate the collection as a private collection (e.g., through one or more user interfaces of the web application). A private collection may only be accessible to specified users and/or via entry of a password. Owner(s) of a private collection may be required to pay a hosting fee (e.g., based on storage size of the collection).

Contributions to Collections

Slide images and their associated metadata are contributed to collections. Contributions may occur in batches and/or on an on-going basis. For example, the initial load of a collection and subsequent additions of significant numbers of slide images may occur in batches or individually. In an embodiment, software modules of server platform 110 provide one or more user interfaces that comprise inputs enabling a contributor to upload a batch of slide images and/or an individual slide image. The uploading of the slide image(s) may also comprise the entry and/or validation of metadata associated with the slide image(s).

Curators

In an embodiment, a collection may be associated with one or more curators, which manage the collection and contributions. A curator is a role that can be assigned to owners (e.g., by default) and/or other designated users (e.g., by an owner). A curator has permissions to contribute or accept contributed slide images into the collection and maintain slide images and metadata in the collection. Curators also have permissions to remove slide images from the collection.

The objective of a curator may be to make the collection more valuable. For example, a curator may increase the value of a collection by improving its ratio of search rating to hosting size. Search ratings may be a function of the usefulness of the metadata that is associated with slide images in the collection or with the collection as a whole. A search rating for a collection may be computed based on a ratio of the number of times that images in the collection are included in search results to the number of images delivered in search results. Additionally or alternatively, the search rating may be based on feedback for slide images in the collection that has been provided by one or more users. For example, the feedback may comprise an indication of whether or not a user found a slide image relevant to his or her search. Storage or hosting size is derived from either the number of slide images in the collection and/or the sizes of the slide images in the collection.

Search Refinement

In an embodiment, search results may be refined using a "warm"/"cold" feedback mechanism. In response to a search request, the web application may deliver search results comprising a user interface that comprises an array of slide image thumbnails. In addition, each slide image thumbnail may be provided in conjunction with at least some of the metadata associated with the corresponding slide image. Hovering over a slide image thumbnail may display a larger preview of the slide image corresponding to the thumbnail. Clicking on a slide image thumbnail may display the corresponding slide image at a higher resolution.

In addition, the search results user interface may comprise a warm/cold input for each slide image thumbnail in the array. The warm/cold input may comprise one or more icons, images, hyperlinks, buttons, or any other type of inputs capable of being selected by a user. In an embodiment, the user can iteratively "tune" search results by clicking on (or, if a touch-screen interface is provided, touching) the warm/cold input adjacent to one or more slide image thumbnails. For instance, the warm/cold input may comprise two inputs, one representing warm, and one representing cold. When a user selects the warm input, coefficients in a search algorithm (e.g., associated with the slide image corresponding to the warm input) are adjusted to make it more likely that the corresponding slide image will be delivered as part of a search result in future search requests with the same or similar search predicate (e.g., keywords). In contrast, when a user selects the cold input, the coefficients may be adjusted in the opposite manner to make it less likely that the corresponding slide image will be delivered in a search result in future search requests with the same or similar search predicate. A user's interactions with the warm/cold inputs of the search results may cause the search results to be immediately updated, and also enables the search algorithms to improve over time via adjustments of weights associated with various search parameters.

In addition to the search algorithms as a whole being tuned according to a warm/cold user-feedback mechanism, separate tuning may also be maintained for individual users. This enables search behavior to be customized to more closely correspond to a given user's search needs.

Figure 2:
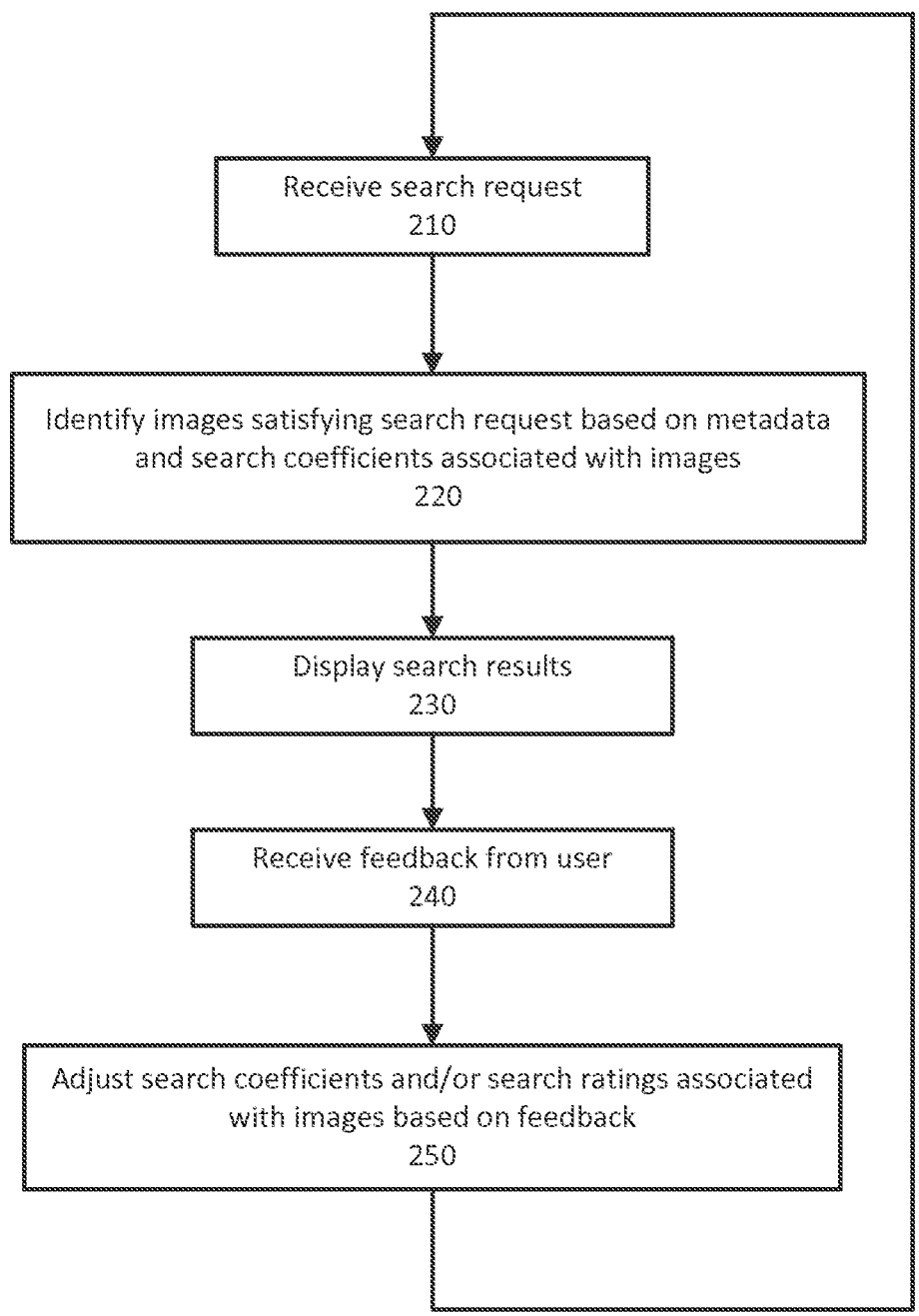
FIG. 2 illustrates a process for improving search results, according to an embodiment.

FIG. 2 illustrates a process for improving search results, according to an embodiment. In step 210, a search request is received from a user. The search request may comprise a search predicate, which may comprise one or more keywords and/or an image. In step 220, images in the repository are identified by comparing the search predicate to metadata and/or images themselves. In addition, these images may be ordered or filtered based on search coefficients associated with the images. In step 230, the search results are displayed to the user, for example, as a grid of thumbnail images with some associated metadata, feedback inputs, and/or hyperlinks (e.g., to external URLs). In step 240, the user may provide feedback for one or more of the images in the search results. The feedback may indicate whether or not the image was an appropriate result for the requested search. In step 250, this feedback is used to adjust the search coefficients and/or search ratings associated with the image(s) that were the subject of the feedback.

Visual Search Algorithm

In an embodiment, the repository makes use of a visual search algorithm, which may be iteratively improved, to enable one or more image regions to be used as a search predicate. The visual search can be based on a wide variety of standard techniques, or on novel techniques. Examples of novel techniques include those disclosed in U.S. Pat. No. 7,257,268, entitled "Systems and Methods for Image Pattern Recognition" and issued Aug. 14, 2007, and U.S. Pat. No. 7,844,125, entitled "Systems and Methods for Image Pattern Recognition" and issued Nov. 30, 2010, which describe methods based on a mathematical technique called vector quantization, and which are both hereby incorporated herein by reference.

The visual search algorithm may implement a stochastic tuning mechanism. This enables it to improve over time from the feedback provided by users, as discussed above. For example, coefficients in the visual search algorithm may be adjusted to make a given slide image more or less likely to be delivered as part of future search results for the same or similar predicate image, based on warm/cold feedback provided by one or more users.

Reputations

In an embodiment, the one or more software modules of server platform 110 may compute a reputation value for each user based on an analysis of the user's contributions and/or curation activities. Reputations may be computed from feedback provided by repository users directly and/or based on the ratings of slide images contributed and/or curated by the user. In addition to being available as a measure of a user's value to the repository, a reputation may be associated with the slide images contributed and/or curated by the user, and used to refine ratings for these slide images to improve search results.

Image Ratings

In an embodiment, as mentioned above, the one or more software modules of server platform 110 may compute a rating for each slide image in the repository. The rating for each slide image may be derived from an analysis of the search activity on the slide image and/or user feedback. For example, the portion of the rating that is based on a slide image's search rating or activity (or in embodiments which utilize just the search activity, the entire rating) may be computed from a ratio of the number of times that the slide image is included in search results to the total number of slide images delivered in those search results. Additionally or alternatively, the rating may be adjusted based on the reputation value of the contributing and/or curating user(s). The rating for a slide image may be used to determine its priority in search results.

Collection Credit

In an embodiment, the computed ratings for each slide image may be used to credit collections or collection owners. Each collection may itself have a rating computed from the average rating of all slide images in the collection. This collection rating can be used to compute the value of the collection, and hence the revenue or expense that it generates for its owner. For example, a value ratio may be computed by dividing the collection rating (e.g., the average slide image rating across the entire collection) by the collection storage size (e.g., the number of slide images in the collection, or the amount of storage space utilized by the slide images in the collection). A higher collection rating or lower storage size increases the value of the collection in the repository, and a lower collection rating or higher storage size decreases the value of the collection in the repository. Depending on this computed value ratio, the owner of the collection may receive revenue from the collection or be forced to pay a hosting fee to maintain the collection. For example, if the computed value ratio is greater than a threshold (e.g., one), then the owner may receive revenue. This revenue may be in proportion to how much greater the value ratio is to the threshold. However, if the computed value ratio is less than the threshold, then the owner may have to pay a hosting fee. This hosting fee may be in proportion to how much lower the value ratio is to the threshold.

Collections as Advertising

In an embodiment, image slides contributed to collections in the repository may include external links as metadata. In other words, the metadata associated with a collection and/or its individual image slides may comprise a reference to a remote location. For example, the reference may comprise a Uniform Resource locator (URL) or hyperlink comprising a URL. The subject of the URL may be a website, mobile application, etc.

In addition, a unique, permanent URL may be associated with each collection and/or each slide image in each collection. Thus, the URL may be embedded (e.g., as a hyperlink) in a website, mobile application, and/or in printed materials, such as textbooks, seminar agendas, and notes.

This bidirectional linking—from the metadata of collections and/or slide images to other sites, and from other sites or printed materials to collections and or slide images—enables content stored as collections in the repository to serve as advertising for external sources of revenue (e.g., by the collection owner). For example, physical specimen libraries (e.g., bio-banks) are a specific case of monetizing a resource by posting digital content in one or more repository collections. References in metadata associated with one or more slide images of a collection can be used to generate hyperlinks to an external web-based "storefront" of a bio-bank. This enables researchers to use the repository to locate and purchase access to physical specimens. For instance, the bio-bank can store a collection of slide images for its physical specimens in the repository. The bio-bank can input references to its Internet storefront into the metadata associated with the collection or individual slide images. Then, search results can display any one or more of these slide images as a thumbnail in association with a hyperlink comprising the reference from the metadata associated with slide image or corresponding collection. Thus, using a standard web browser, a user viewing the search results may click on a hyperlink associated with a particular slide image. This will cause the web browser to request and receive one or more web pages from the bio-bank storefront (e.g., from a web server serving the storefront). The hyperlink may comprise a URL that is associated with the particular specimen represented by the particular slide image, in which case the user may be directed to a web page that is specific to the particular physical specimen, and through which the user may locate and/or purchase access to the physical specimen. In such a case, the operator of the repository may collect a referral fee for each followed link from a slide image in the repository to a physical specimen library that results in sales of a physical specimen. It should be understood that such referral fees may be tracked and charged automatically by the one or more software modules of server platform 110.

Image Analysis Algorithms

In an embodiment, the repository may host one or more image analysis algorithms. These image analysis algorithms may be provided by third parties. For instance, the image analysis algorithms may be provided from third parties via one or more open APIs. The image analysis algorithms may be used to extract searchable information from the repository, for example, by developing information from the images that is stored in their associated metadata. This developed information may then be subsequently searched using the repository search engine. In addition to enhancing the functionality of the repository for end users, the hosting of image analysis algorithms also provides image analysis developers with a useful platform for developing, testing, and marketing their applications.

Image analysis algorithms may be developed to extract and specify information from images, such as identifying objects, counting objects, rare event detection, stain quantification, and various types of pattern recognition. An example would be applications for the quantification of images made from immunochemistry specimens for the purpose of scoring breast cancer prognostic indicators, such as ER, PR, and Her2.

Online Peer Review

In an embodiment, the one or more software modules may associate a slide image or group of slide images (e.g., cases, seminars, or collections) with a "peer reviewed" status or designation. The "peer reviewed" status may be set or updated by owners and/or curators, reflecting external review processes. The distinction of "peer reviewed" is important in scientific communities and reflects the collaborative nature of image metadata such as medical diagnoses.

Additionally or alternatively, the repository may provide a mechanism for collection owners and/or curators to submit a slide image or group of slide images for review. In an embodiment, the one or more software modules of server platform 110 may implement a routing, rating, and commenting process to enable procedural designation of submitted slide images or groups of slide images as having been "peer reviewed."

The peer review process may comprise identifying groups of users as experts for classes of images or cases, and then routing cases which have been identified as candidates for peer review to a sequence of experts to solicit their approval or feedback of the associated metadata, such as interpretation, description, or diagnosis associated with the images or cases.

Figure 3:
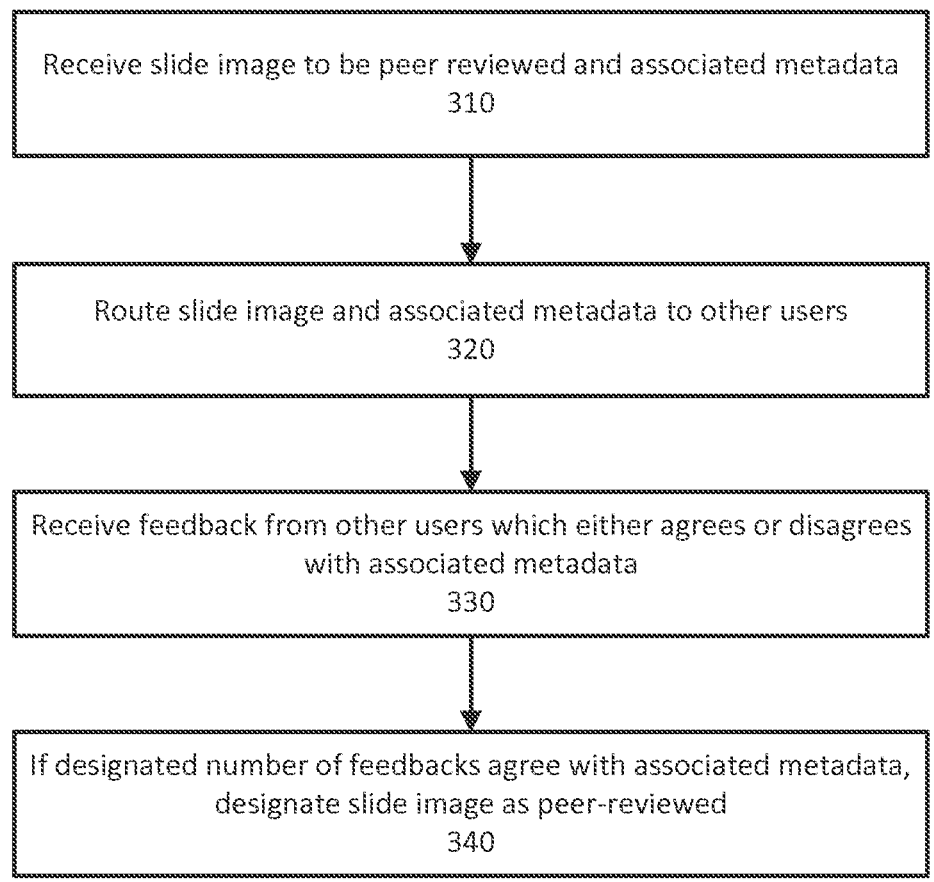
FIG. 3 illustrates a process for peer reviewing a slide image, according to an embodiment.

FIG. 3 illustrates a process for peer reviewing one or more slide images, according to an embodiment. In step 310, a slide image to be peer reviewed and its associated metadata are received from a contributing user. The slide image and its associated metadata may be routed to one or more users in step 320. These users may be designated by the contributing user and/or selected by the system based on their reputations, qualifications, etc. In step 330, one or more of the selected users provide feedback. The feedback may indicate either that the user agrees with metadata (e.g., a diagnosis and/or characterization) associated with the slide image, or disagrees with the associated metadata. The process keeps track of the number of agreements received, and/or the number of disagreement received for the slide image. If the number of agreements or ratio of agreements to disagreements exceeds a predetermined threshold, then the slide image and/or associated metadata is designated with the status of "peer reviewed" (e.g., in the associated metadata).

Cross-Referencing of Owners of Collections

Collections stored in the repository may be owned by individuals who are members of online social networks, such as Facebook™, Google+™ or LinkedIn™. In an embodiment, the repository can cross-reference such owners, enabling their associates in such social networks to be notified of their activity within the repository, such as contributions of new images and information or updates to existing metadata. For example, one or more software modules of server platform 110 may interface with one or more social networks via one or more APIs (e.g., Facebook Connect™) to implement this cross-referencing.

Cross-Referencing of Users

In addition, any user of the repository may be a member of online social networks, such as Facebook™, Google+™ or LinkedIn™. In an embodiment, the repository can cross-reference such users, enabling their activities within the repository to be communicated to their associates in such social networks. Such activities may include, without limitation, search requests, search results (e.g., designated as being of special interest), messages sent to an owner of a collection in the repository, peer reviews performed, and/or creation of saved image sets. For example, one or more software modules of server platform 110 may interface with one or more social networks via one or more APIs (e.g., Facebook Connect™) to implement this cross-referencing.

Example Use as Archive for Consultation Cases

In one illustrative, non-limiting application, the disclosed online image repository may be used as a robust and inexpensive archive for consultation cases. As each of one or more consultants reviews cases, the cases may be contributed to the image repository as elements of the consultant's online collection. Private information, such as personal health information (PHI), can continue to be stored on the consultant's local system with inbound links from the consultant's local system to the images in the repository. This enables consultants to store very large pathology images in the repository, rather than on their local systems, and may even generate revenue for the consultants (e.g., depending on the computed value of the consultants' collections). In addition, the value of the images that the consultants contribute enhances the repository. Consultation cases tend to be rare and unusual, which is why they have been referred to a consultant in the first place. The combination of a rare and unusual case with expert diagnostic interpretation (as given by the consultant) may make for a valuable contribution to the repository as an online decision support resource.

Example Use as Long-Term Archive

In another illustrative, non-limiting application, the disclosed online image repository may be used as a robust and inexpensive archive for routine clinical imaging. Typically, active cases are maintained on local systems in pathology and hospital labs. After a designated period of time, cases may be uploaded to the repository as contributions to a collection. Private information, such as PHI, can continue to be stored on the local system with inbound links from the local system to the images in the repository. This enables clinical systems to store very large pathology images in the repository, rather than on their local systems, and may even generate revenue for the labs (e.g., depending on the computed value of the labs' collections). In addition, the value of the images that the labs contribute enhances the repository.

Example Scanning Devices

In an embodiment, the disclosed methods and systems may utilize digital scanning technologies, as disclosed in U.S. Pat. No. 6,711,283, entitled "Fully Automatic Rapid Microscope Slide Scanner" and issued Mar. 23, 2004, U.S. Pat. No. 6,917,696, entitled "Fully Automatic Rapid Microscope Slide Scanner" and issued Jul. 12, 2005, U.S. Pat. No. 7,457,446, entitled "Fully Automatic Rapid Microscope Slide Scanner" and issued Nov. 25, 2008, U.S. Pat. No. 8,055,042, entitled "Fully Automatic Rapid Microscope Slide Scanner" and issued Nov. 8, 2011, U.S. Pat. No. 7,978,894, entitled "Fully Automatic Rapid Microscope Slide Scanner" and issued Jul. 12, 2011, and U.S. patent application Ser. No. 13/291,971, entitled "Fully Automatic Rapid Microscope Slide Scanner" and filed Nov. 8, 2011, all of which are hereby incorporated herein by reference.

Example Processing Device

Figure 4:
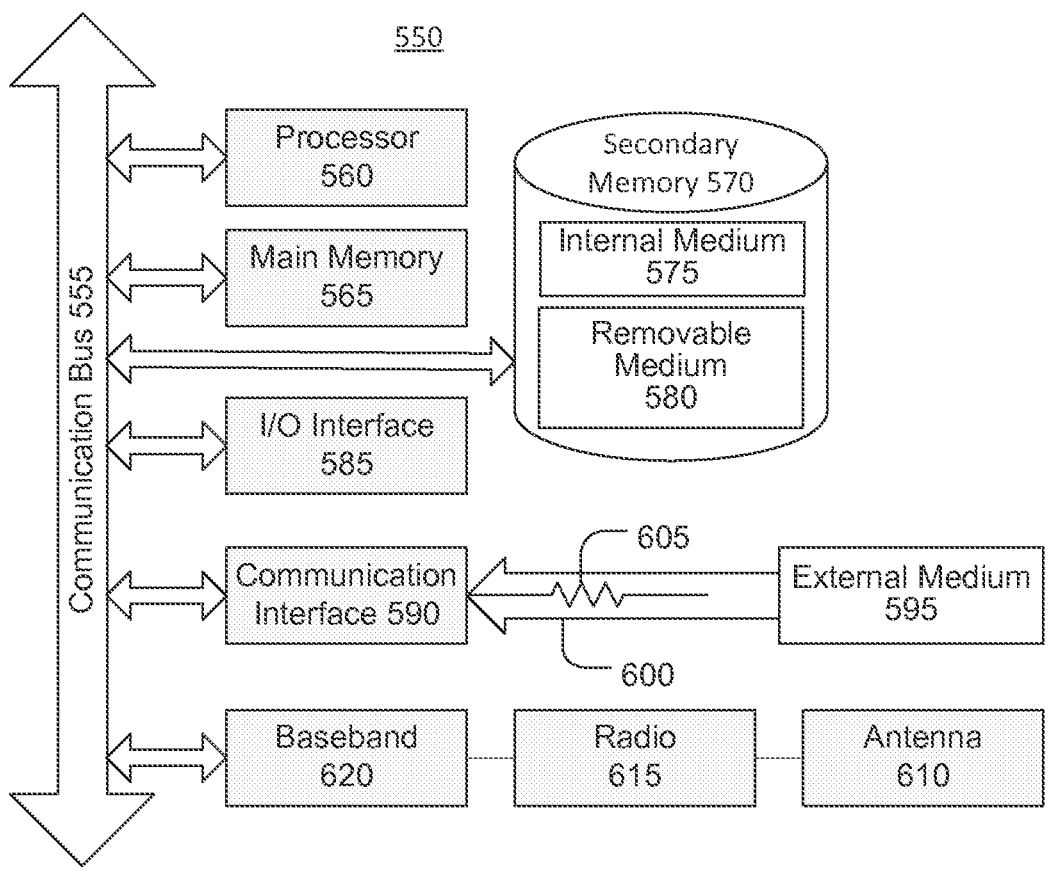
FIG. 4 illustrates a processing system on which one or more of the processes described herein may be executed, according to an embodiment.

FIG. 4 is a block diagram illustrating an example wired or wireless system 550 that may be used in connection with various embodiments described herein. For example the system 550 may be used as or in conjunction with one or more of the modules described herein, and/or as server platform 110 or user system(s) 130. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the main memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that were previously described with respect to FIGS. 2 and 3.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A system comprising:
    a memory storing an image repository, the image repository comprising a plurality of collections, wherein each of the plurality of collections comprises one or more digital slide images and associated metadata; and
    at least one hardware processor configured to
        associate each of the plurality of collections with a collection rating,
        for each of a plurality of search requests,
            identify one or more digital slide images based on at least the search request,
            provide a graphical user interface providing access to each of the identified one or more digital slide images to a user along with an associated input for each of the identified one or more digital slide images,
            receive user feedback via the input for at least one of the identified one or more digital slide images, and
            update the collection rating, associated with the collection that comprises the at least one digital slide image, based on the user feedback for the at least one digital slide image,
        compute a value for each of the plurality of collections based on a ratio of the associated collection rating to a current size of the collection, and,
        for each of the plurality of collections, facilitate either payment to an owner of the collection or charging of the owner of the collection based on the computed value by,
            when the computed value is above a threshold, initiating payment to the owner of the collection in proportion to how much greater the computed value is to the threshold, and,
            when the computed value is below the threshold, initiating charging of the owner of the collection in proportion to how much lower the computed value is to the threshold.

2. The system of claim 1, wherein the input for each of the identified one or more digital slide images comprises a warm input and a cold input, and wherein updating the collection rating comprises:
    increasing the collection rating when the user feedback is selection of the warm input; and
    decreasing the collection rating when the user feedback is selection of the cold input.

3. The system of claim 1, wherein the at least one hardware processor is further configured to, for each of the plurality of search requests, adjust one or more weights in a search algorithm, used to identify digital slide images based on search requests, based on the user feedback for the at least one digital slide image.

4. The system of claim 3, wherein the input for each of the identified one or more digital slide images comprises a warm input and a cold input, and wherein adjusting the one or more weights in the search algorithm comprises:
    increasing a likelihood that the at least one digital slide image is returned in response to a similar search request when the user feedback is selection of the warm input; and
    decreasing a likelihood that the at least one digital slide image is returned in response to a similar search request when the user feedback is selection of the cold input.

5. The system of claim 1, wherein providing access to the identified one or more digital slide images to a user comprises:
    if the user is not a subscriber, providing access to the identified one or more digital slide images at a first resolution; and,
    if the user is a subscriber, providing access to the identified one or more digital slide images at a second resolution that is higher than the first resolution.

6. The system of claim 5, wherein providing access to the identified one or more digital slide images to a user further comprises, if the user is not a paying user, prompting the user to pay a transaction fee to view the identified one or more digital slide images at the second resolution or to become a subscriber.

7. The system of claim 1, wherein one or more of the associated metadata comprise one or more references to external data.

8. The system of claim 7, wherein the one or more references to external data comprise a uniform resource locator (URL) to an external web-based store, and wherein, for each of the plurality of search requests, the graphical user interface further provides access to each URL in the associated metadata for each of the identified one or more digital slide images.

9. The system of claim 1, wherein each of the plurality of search requests comprises an image region, and wherein identifying one or more digital slide images based on at least the search request comprises utilizing the image region as a search predicate.

10. The system of claim 1, wherein the at least one hardware processor is further configured to interface with one or more image analysis tools, and wherein the one or more image analysis tools are configured to extract and enhance metadata associated with the one or more digital slide images.

11. The system of claim 10, wherein the one or more image analysis tools are hosted on one or more third-party systems, and wherein the interface with the one or more image analysis tools comprises an application programming interface (API).

12. The system of claim 1, wherein the at least one hardware processor is further configured to provide peer review by:
    receiving a set of one or more digital slide images to be peer reviewed and associated metadata from a contributing user;
    routing the set of one or more digital slide images and the associated metadata to a plurality of other users;
    receiving feedback from each of one or more of the plurality of other users, wherein each feedback comprises either an agreement with the associated metadata or a disagreement with the associated metadata;

determining whether a designated number of the received feedbacks comprise the agreement with the associated metadata; and, if it is determined that the designated number of the received feedbacks comprise the agreement with the associated metadata, associating a peer-reviewed status with the set of one or more digital slide images.

13. The system of claim 1, wherein the threshold is equal to one.

14. The system of claim 1, wherein, for each of the plurality of collections, the associated collection rating is based on a ratio of a number of times that the one or more digital slide images in the collection are included in search results to a number of total digital slide images included in the search results.

15. The system of claim 1, wherein the at least one hardware processor is further configured to, for each of the plurality of collections, compute a reputation for a curator of the collection based on the user feedback received for the one or more digital slide images in the collection.

16. The system of claim 1, wherein the at least one hardware processor is further configured to compute an image rating for each of the one or more digital slide images in each of the plurality of collections.

17. The system of claim 16, wherein, for each of the one or more digital slide images in each of the plurality of collections, the image rating is computed based on a ratio of a number of times that the digital slide image is included in search results to a number of total digital slide images included in the search results.

18. The system of claim 1, wherein one or more of the associated metadata comprise a diagnostic interpretation from a consultation.

19. A method of using at least one hardware processor, the method comprising:

storing an image repository in a memory, the image repository comprising a plurality of collections, wherein each of the plurality of collections comprises one or more digital slide images and associated metadata;

associating each of the plurality of collections with a collection rating;

for each of a plurality of search requests, identifying one or more digital slide images based on at least the search request, providing a graphical user interface providing access to each of the identified one or more digital slide images to a user along with an associated input for each of the identified one or more digital slide images, receiving user feedback via the input for at least one of the identified one or more digital slide images, and updating the collection rating, associated with the collection that comprises the at least one digital slide image, based on the user feedback for the at least one digital slide image;

computing a value for each of the plurality of collections based on a ratio of the associated collection rating to a current size of the collection; and, for each of the plurality of collections, facilitating either payment to an owner of the collection or charging of the owner of the collection based on the computed value by, when the computed value is above a threshold, initiating payment to the owner of the collection in proportion to how much greater the computed value is to the threshold, and, when the computed value is below the threshold, initiating charging of the owner of the collection in proportion to how much lower the computed value is to the threshold.

20. A non-transitory computer-readable medium having instructions stored thereon, wherein the instructions, when executed by a processor, cause the processor to:

store an image repository in a memory, the image repository comprising a plurality of collections, wherein each of the plurality of collections comprises one or more digital slide images and associated metadata;

associate each of the plurality of collections with a collection rating;

for each of a plurality of search requests, identify one or more digital slide images based on at least the search request, provide a graphical user interface providing access to each of the identified one or more digital slide images to a user along with an associated input for each of the identified one or more digital slide images, receive user feedback via the input for at least one of the identified one or more digital slide images, and update the collection rating, associated with the collection that comprises the at least one digital slide image, based on the user feedback for the at least one digital slide image;

compute a value for each of the plurality of collections based on a ratio of the associated collection rating to a current size of the collection; and, for each of the plurality of collections, facilitate either payment to an owner of the collection or charging of the owner of the collection based on the computed value by, when the computed value is above a threshold, initiating payment to the owner of the collection in proportion to how much greater the computed value is to the threshold, and, when the computed value is below the threshold, initiating charging of the owner of the collection in proportion to how much lower the computed value is to the threshold.

* * * * *